United States Patent
Palkon et al.

(10) Patent No.: US 7,007,696 B2
(45) Date of Patent: Mar. 7, 2006

(54) MASK CUSHION AND METHOD OF USING SAME

(75) Inventors: David J. Palkon, Tinley Park, IL (US); Geoffrey P. Sleeper, Bay Village, OH (US); Norbert E Cichon, Tinley Park, IL (US); James L. Fitzsimmons, Schererville, IN (US)

(73) Assignee: Tiara Medical Systems, Inc., Oak Forest, IL (US)

( * ) Notice: Subject to any disclaimer, the term of this patent is extended or adjusted under 35 U.S.C. 154(b) by 606 days.

(21) Appl. No.: 10/147,616

(22) Filed: May 16, 2002

(65) Prior Publication Data

US 2003/0019495 A1   Jan. 30, 2003

Related U.S. Application Data

(60) Provisional application No. 60/291,902, filed on May 18, 2001, provisional application No. 60/314,141, filed on Aug. 22, 2001.

(51) Int. Cl.
*A62B 18/02* (2006.01)

(52) U.S. Cl. .......................... 128/207.13; 128/206.24; 128/206.26

(58) Field of Classification Search ........... 128/205.25, 128/206.24, 206.26, 207.13
See application file for complete search history.

(56) References Cited

U.S. PATENT DOCUMENTS

| | | |
|---|---|---|
| 781,516 A | 12/1905 | Guthrie, Jr. |
| 812,706 A | 2/1906 | Warbasse |
| 1,081,745 A | 12/1913 | Johnston et al. |
| 1,192,186 A | 7/1916 | Greene |
| 1,653,572 A | 12/1927 | Jackson |
| 1,710,160 A | 4/1929 | Gibbs |
| 1,926,027 A | 9/1933 | Biggs |
| 2,123,353 A | 7/1938 | Catt |
| 2,130,555 A | 9/1938 | Malcom |
| 2,133,699 A | 10/1938 | Heidbrink |
| 2,166,164 A * | 7/1939 | Lehmberg .............. 128/206.24 |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,428,451 A | 10/1947 | Emerson |
| 2,438,058 A | 3/1948 | Kincheloe |
| 2,578,621 A | 12/1951 | Yant |

(Continued)

FOREIGN PATENT DOCUMENTS

DE    196 03 949    8/1997

(Continued)

*Primary Examiner*—Aaron J. Lewis
(74) *Attorney, Agent, or Firm*—Pearne & Gordon LLP (57) ABSTRACT

A nasal CPAP treatment apparatus is disclosed with a flow generator coupled to a nasal mask. The mask has a nasal cushion forming a nose-receiving cavity. The cushion has a triangularly-shaped frame of resilient material with a mask engaging portion connected by a side wall to a face engaging portion which has a nasal bridge region, a cheek region and a lip region. The cushion may have a portion of the side wall in the nasal bridge region being other than straight to provide an improved sealing in the nasal bridge region. A plurality of membranes, preferably three, of resilient material extend substantially around the triangularly-shaped frame. Some of the membranes are thicker in the lip region than in the nasal bridge region to improve fit of the cushion in use.

44 Claims, 7 Drawing Sheets

U.S. PATENT DOCUMENTS

| | | | |
|---|---|---|---|
| 2,625,155 A | 1/1953 | Engelder | |
| 2,706,983 A | 4/1955 | Matheson et al. | |
| RE24,193 E | 8/1956 | Emerson | |
| 2,931,356 A | 4/1960 | Schwarz | |
| D188,084 S | 5/1960 | Garelick | |
| 2,939,458 A * | 6/1960 | Lundquist | 128/206.25 |
| 3,013,556 A | 12/1961 | Galleher | |
| 3,182,659 A | 5/1965 | Blount | |
| 3,189,027 A | 6/1965 | Bartlett | |
| 3,193,624 A | 7/1965 | Webb et al. | |
| 3,238,943 A | 3/1966 | Holley | |
| 3,315,674 A | 4/1967 | Bloom et al. | |
| 3,330,273 A * | 7/1967 | Bennett | 128/206.26 |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | |
| 3,700,000 A | 10/1972 | Hesse | |
| 3,720,235 A | 3/1973 | Schrock | |
| 3,796,216 A | 3/1974 | Schwarz | |
| 3,799,164 A | 3/1974 | Rollins | |
| D231,803 S | 6/1974 | Huddy | |
| 4,069,516 A | 1/1978 | Watkins, Jr. | |
| 4,077,404 A | 3/1978 | Elam | |
| D250,131 S | 10/1978 | Lewis et al. | |
| 4,167,185 A * | 9/1979 | Lewis | 128/206.24 |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,328,797 A | 5/1982 | Rollins, III | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,467,799 A | 8/1984 | Steinberg | |
| 4,522,639 A | 6/1985 | Ansite et al. | |
| 4,558,710 A | 12/1985 | Eichler | |
| D285,496 S | 9/1986 | Berman | |
| 4,616,647 A | 10/1986 | McCreadie | |
| 4,622,964 A | 11/1986 | Flynn | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A * | 7/1987 | Wilcox | 128/206.24 |
| H397 H * | 1/1988 | Stark | 128/206.24 |
| D293,613 S | 1/1988 | Wingler | |
| 4,739,755 A * | 4/1988 | White et al. | 128/206.12 |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,938,210 A | 7/1990 | Shene | |
| 4,938,212 A | 7/1990 | Snook et al. | |
| 4,944,310 A | 7/1990 | Sullivan | |
| D310,431 S | 9/1990 | Bellm | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Häkkinen | |
| 5,069,205 A | 12/1991 | Urso | |
| 5,074,297 A | 12/1991 | Venegas | |
| D323,908 S | 2/1992 | Holister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,980 A | 8/1992 | Haughey et al. | |
| 5,140,982 A | 8/1992 | Bauman | |
| 5,159,938 A | 11/1992 | Laughlin | |
| 5,178,138 A | 1/1993 | Walstrom et al. | |
| D334,633 S | 4/1993 | Rudolph | |
| 5,231,983 A | 8/1993 | Matson et al. | |
| 5,233,978 A | 8/1993 | Callaway | |
| 5,243,971 A | 9/1993 | Sullivan et al. | |
| 5,265,595 A * | 11/1993 | Rudolph | 128/204.18 |
| 5,279,289 A | 1/1994 | Kirk | |
| 5,280,784 A | 1/1994 | Köhler | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,349,949 A | 9/1994 | Schegerin | |
| 5,357,951 A | 10/1994 | Ratner | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A | 8/1996 | Lomas | |
| 5,546,936 A | 8/1996 | Virag et al. | |
| 5,558,090 A | 9/1996 | James | |
| RE35,339 E | 10/1996 | Rapoport | |
| 5,560,354 A | 10/1996 | Berthon-Jones | |
| 5,570,682 A | 11/1996 | Johnson | |
| 5,570,689 A * | 11/1996 | Starr et al. | 128/207.11 |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,662,101 A | 9/1997 | Ogden et al. | |
| 5,666,946 A | 9/1997 | Langenback | |
| 5,685,296 A | 11/1997 | Zdrojkowski | |
| 5,687,715 A | 11/1997 | Landis et al. | |
| 5,715,814 A | 2/1998 | Ebers | |
| 5,746,201 A | 5/1998 | Kidd | |

| | | | | | | |
|---|---|---|---|---|---|---|
| 5,813,423 | A | 9/1998 | Kirchgeorg | 6,772,760 B1 | 8/2004 | Frater et al. |
| 5,832,918 | A | 11/1998 | Pantino | 6,871,649 B1 * | 3/2005 | Kwok et al. ............ 128/206.24 |
| 5,921,239 | A | 7/1999 | McCall et al. | 2002/0020416 A1 | 2/2002 | Namey |
| 6,016,804 | A | 1/2000 | Gleason et al. | 2002/0029780 A1 | 3/2002 | Frater et al. |
| 6,019,101 | A * | 2/2000 | Cotner et al. ........... 128/207.13 | 2004/0144386 A1 | 7/2004 | Frater et al. |
| 6,044,844 | A | 4/2000 | Kwok et al. | | | |
| 6,112,746 | A * | 9/2000 | Kwok et al. ........... 128/207.13 | | | |
| 6,119,693 | A | 9/2000 | Kwok et al. | | | |

FOREIGN PATENT DOCUMENTS

| | | |
|---|---|---|
| 6,192,886 B1 * | 2/2001 | Rudolph ................ 128/207.13 |
| 6,357,441 B1 * | 3/2002 | Kwok et al. ........... 128/207.13 |
| 6,412,488 B1 | 7/2002 | Barnett et al. |
| 6,467,483 B1 | 10/2002 | Kopacko et al. |
| 6,513,526 B1 | 2/2003 | Kwok et al. |
| 6,530,373 B1 * | 3/2003 | Patron et al. ........... 128/205.25 |
| 6,634,358 B1 * | 10/2003 | Kwok et al. ........... 128/205.25 |
| 6,701,927 B1 * | 3/2004 | Kwok et al. ........... 128/207.13 |

| | | |
|---|---|---|
| EP | 0 334 555 | 9/1989 |
| EP | 0 303 090 | 4/1992 |
| EP | 0 747 078 | 10/2002 |
| EP | 0 853 962 | 3/2004 |
| JP | 11-397 | 1/1999 |
| WO | 01/62326 | 8/2001 |

* cited by examiner

MASK CUSHION AND METHOD OF USING SAME

RELATED APPLICATIONS

This application, pursuant to 37 C.F.R. § 1.78(c), claims priority based on provisional application Ser. No. 60/291,902 filed May 18, 2001 and provisional application Ser. No. 60/314,141 filed Aug. 22, 2001.

FIELD OF THE INVENTION

The present invention relates to an improved cushion that contacts a portion of a patient's face to provide a comfortable interface and improved seal between an external device, such as a respiratory mask, and the patient.

DESCRIPTION OF RELATED ART

A variety of respiratory masks are known having a flexible seal that covers the area surrounding the nose and/or mouth of a human user and that are designed to create a continuous seal against the user's face.

Because of the sealing effect created, gases can be provided at a positive pressure within the mask for consumption by the user. The uses of such masks include, but are not limited to high altitude breathing (aviation applications), swimming, mining and fire fighting applications along with various medical diagnostic and therapeutic applications.

One requisite of many of these masks, particularly medical respiratory masks, is that they provide an effective seal against the user's face to prevent leakage of the gas being supplied. Commonly, in conventional mask configurations, the mask-to-face seal has been attained in many instances only with considerable discomfort for the user. This problem is most crucial in those applications, especially medical applications, which require the user to wear the mask continuously for hours or perhaps even days. In such situations, the user will not tolerate an uncomfortable mask for long durations and optimum therapeutic or diagnostic objectives will not be achieved if imperfect seals are formed, or will be achieved with great difficulty and considerable user discomfort.

BACKGROUND OF THE INVENTION

Nasal masks are commonly used in the treatment of respiratory conditions and sleep disorders (e.g., obstructive sleep apnea) by delivering a flow of breathable gas for, or to assist patient respiration. These nasal masks typically receive a gas supply line which delivers gas into a chamber formed by walls of the mask and the user's face. The walls usually are semi-rigid and have a face contacting portion including an aperture which is aligned with the wearer's nostrils. The face contacting portion can comprise a soft, resilient elastometric material which may conform to varius facial contours. The mask normally is secured to the wearer's head by straps. The straps are adjusted to pull the mask against the face with sufficient force to achieve a gas tight seal between the mask and the wearer's face but not so tight as to be uncomfortable. Gas is thus delivered to the mask and into the wearer's nasal passages.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is the face contacting portion may apply excessive pressure to the wearer's face resulting in discomfort and possibly skin irritation. This can occur because the face contacting portion has to distort beyond its normal range of elasticity to conform to certain facial contours which requires the application of excessive forces. In some cases these excessive pressures and forces may cause the face to distort to conform with the face contacting portion to increase wearer discomfort, resulting in facial soreness and ulceration.

An example of the respiratory mask useful in the CPAP treatment is in U.S. Pat. No. 6,112,746 issued to Kwok et al. Sep. 5, 2000, the entire disclosure of which is incorporated by reference. That patent lists over 200 pieces of prior art generally pertinent to the subject invention. The present invention relates to a cushion for a respiratory mask which is more comfortable and provides a superior seal than heretofore available.

These and other advantages will be described in more detail below.

SUMMARY OF THE INVENTION

Accordingly, it is an object of the present invention to provide an improved cushion effecting an superior seal for confronting engagement with the surface of the users face to form a sealed interface therewith that overcomes the shortcomings of conventional seal techniques. This object is achieved, according to one embodiment of the present invention, by providing a cushion in which three membranes are used to provide superior sealing characteristics while minimizing the head strap tension and therefore the compressive forces exerted by the mask against the user's face.

Another object of the present invention is to provide a respiratory mask with an improved cushion wherein the cushion is provided with membranes having variable thicknesses between the nasal bridge region and the region that fits between the nares and the upper lip to provide superior sealing characteristics.

Yet another object of the invention is to provide a mask cushion having a side wall that is other than straight, such as curved or sinuous, which makes the cushion nose compressible to better fit around the user's face.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figure 1:
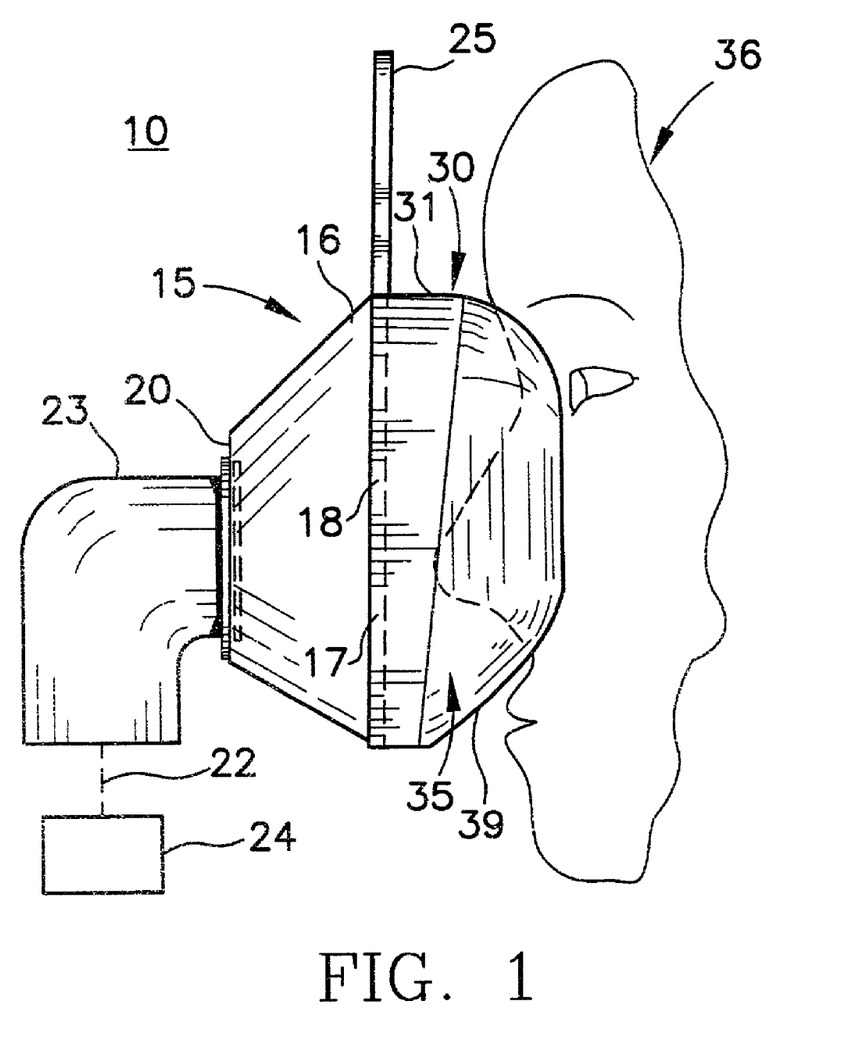
FIG. 1 is a side elevational view of a respiratory mask in accordance with the present invention placed against the face of the user.
Figure 2:
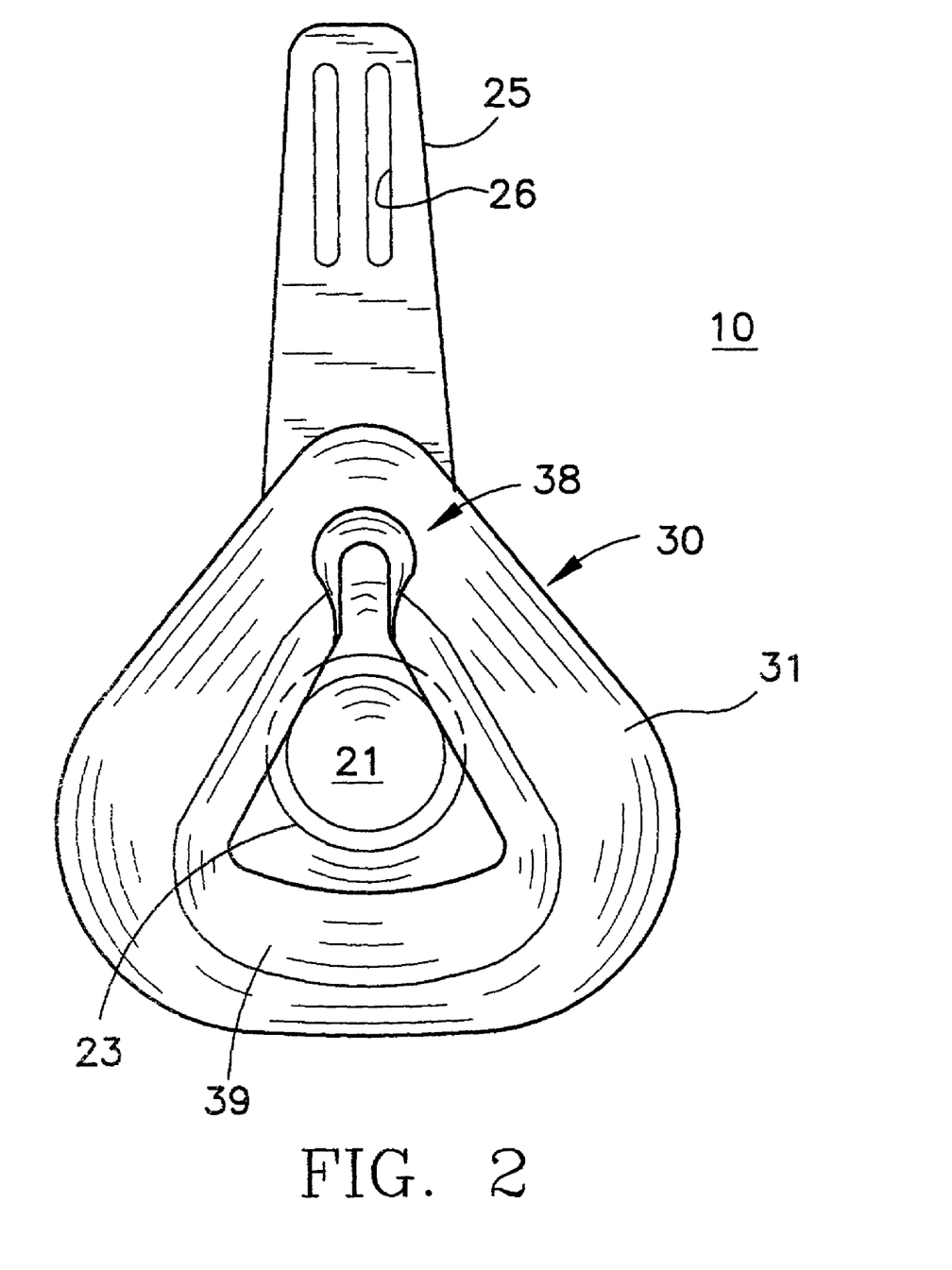
FIG. 2 is a front elevational view of the face side of the respiratory mask including the improved cushion of the present invention.
Figure 3:
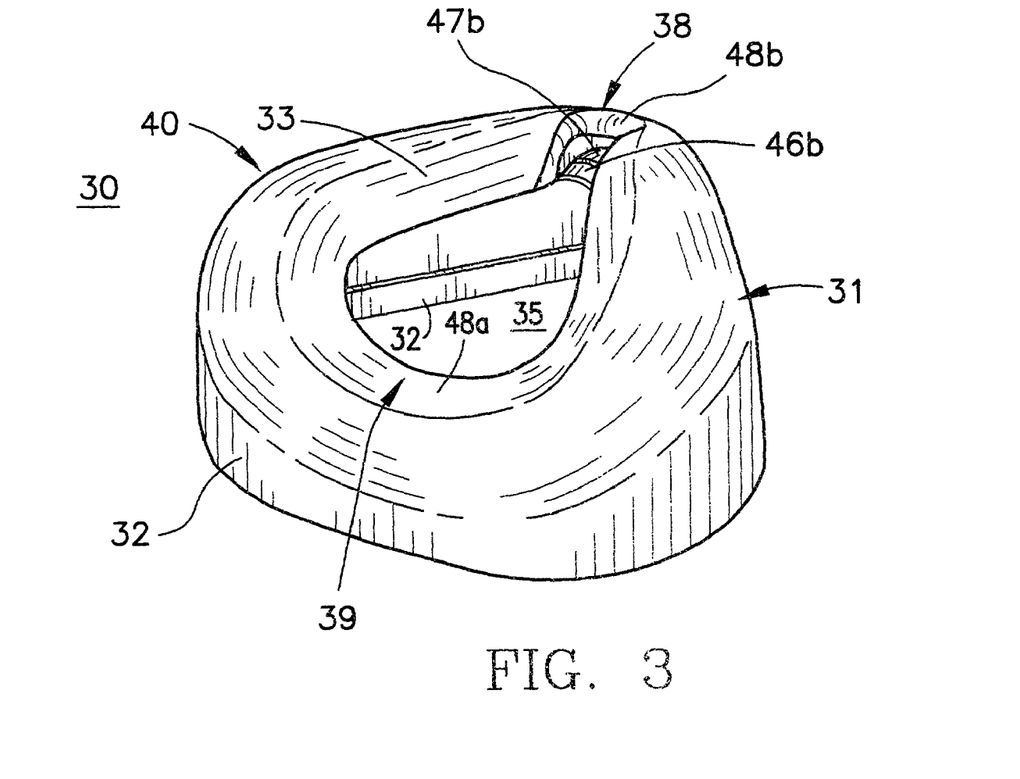
FIG. 3 is a perspective view of an embodiment of the improved cushion.

Referring now to the drawings and particularly FIGS. 1 and 2, there is shown a respiratory mask 10 which includes a rigid shell or cone 15 having a body portion 16. The body portion 16 in plan view is triangular in shape in order to fit the contours of a person's face above the nose to between the nose and the lips. The body portion has a rim 17 with outwardly extending tabs 18 for use with head straps to hold the mask to the users face which are not shown. The cone 15 has an end 20 defining a circular opening 21 to which is coupled a conduit 22 shown by broken line which connects a coupling 23 to the cone 15 and a gas source and flow generator 24. Upwardly extending from the cone 15 is a tab or frame member 25 having parallel vertically disposed slots 26 to accommodate portions of the head straps (not shown but well known in the art) which are used to affix the respiratory mask 10 to the user 36.

Referring now to FIGS. 3–8, there is shown a cushion 30 including the inventive seals or membranes for use in the respiratory mask 10 of the present invention. The cushion 30 includes an outer surface 31 having a frame engaging portion 32 around the bottom periphery thereof and a face engaging portion 33. The cushion 30 defines a chamber 35 between the user 36 and the cone 15.

The cushion 30 further includes a nasal bridge region 38 positioned in use above the user's nose at the bridge portion thereof and a lip region 39 generally positioned in use between the nares of the nose and the lips. A cheek region 40 separates the nasal bridge region 38 and the lip region 39. The frame engaging portion 32 is relatively thick compared to the rest of the cushion 30 and defines a channel 41 in the frame engaging portion 32, the cushion 30 having a bottom surface 42 extending around the channel 41 being defined by an inner lip portion 43 and the side wall 45 extending upwardly from the bottom surface 32 of the cushion. The channel 41 is sized to fit around the rim 17 of the rigid shell or cone 15 in order to securely mount the cushion 30 to the cone or shell 15.

Figure 4:
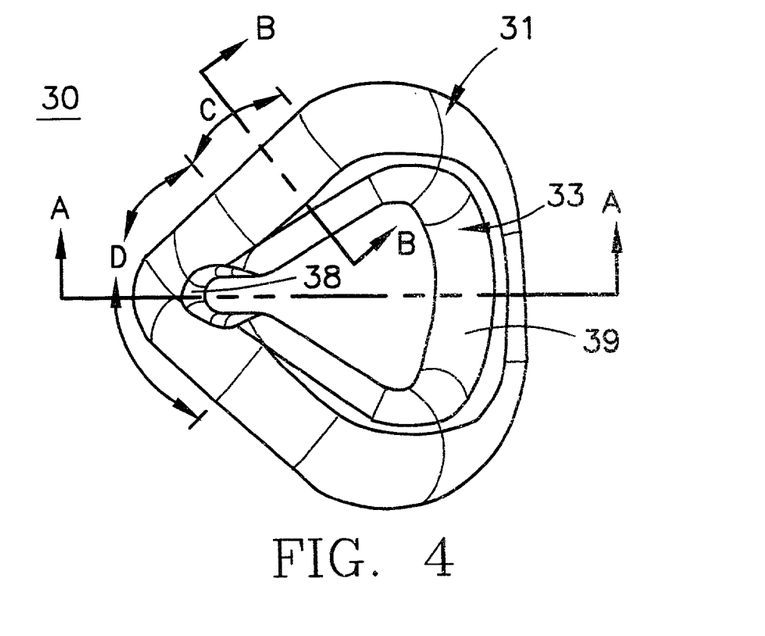
FIG. 4 is a perspective view of a cushion embodying the present invention.
Figure 5:
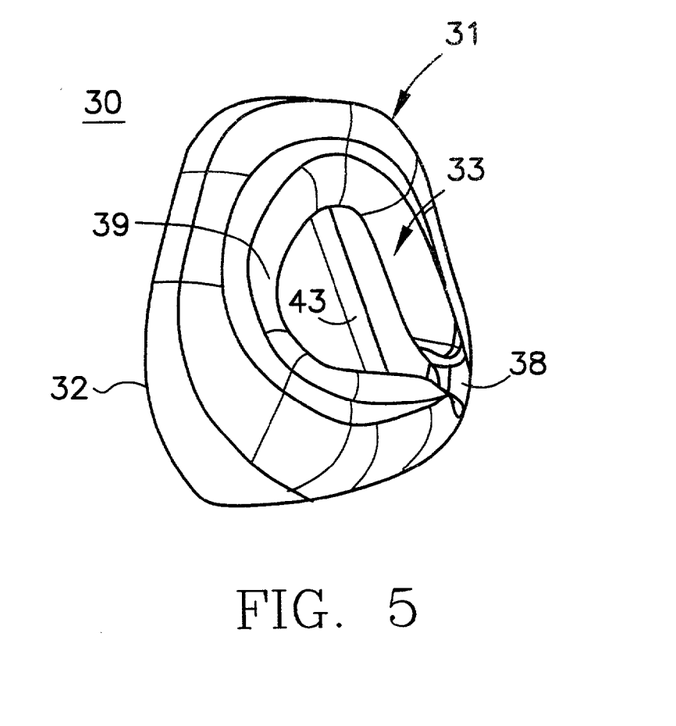
FIG. 5 is a view like FIG. 4 rotated with respect to FIG. 4.
Figure 6:
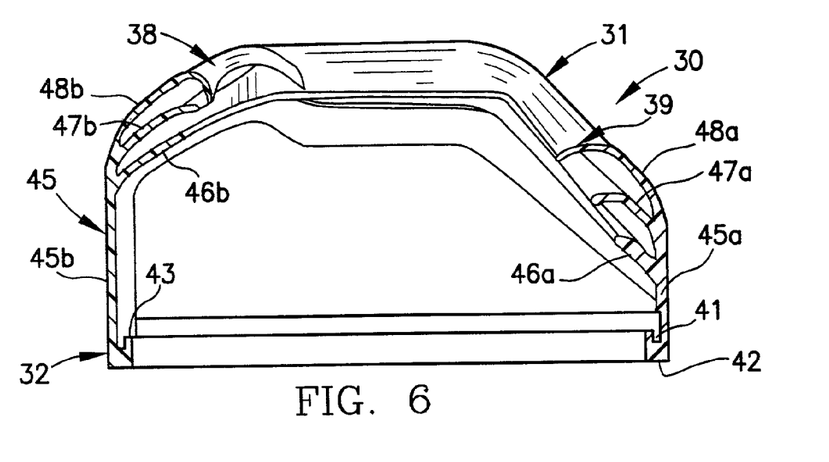
FIG. 6 is a cross-sectional view of one embodiment of the present invention as viewed along line A—A of FIG. 4.
Figure 7:
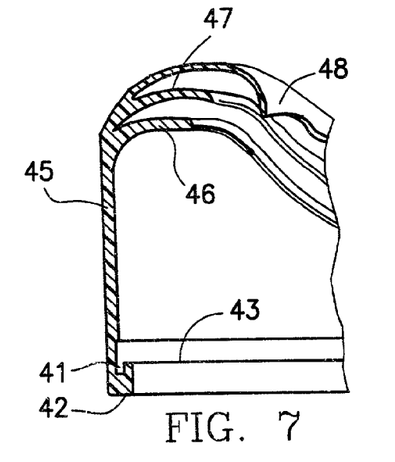
FIG. 7 is a cross-sectional view of one embodiment of the present invention as seen along line B—B of FIG. 4.

Referring to FIGS. 6–7, there is shown a first embodiment of the present invention in which the side wall 45a near the lip region 39 of the cushion 30 is shorter than the side wall 45b near the nasal bridge region 38 of the cushion 30 to provide a better fitting cushion. Near the lip region 39 of the cushion 30 there are three membranes integral with the side wall 45 and extending therefrom, the membranes being denoted as 46a, 47a and 48a. The membrane 46a is the thickest of the three membranes at the lip region 39 of the cushion 30. The membrane 47a is thinner than the membrane 46a at the lip region 39 and thicker than the outermost membrane 48a. The membranes 46, 47, and 48 all have flexibility and deform when a force is applied against the cushion 30 when the cushion is in place against the users face 36, as seen in FIG. 1. The use of three or more membranes is an improvement over the use of two membranes commonly used and seems to provide significant advances in comfort for the user. In the embodiment of FIGS. 6 and 7, the thicknesses of the membranes 46, 47 and 48 change between the lip region 39 of the cushion 30 and the nasal bridge region 38 of the cushion 30. The membranes 46b, 47, and 48b at the nasal bridge region 38 of the cushion 30 are all about the same thickness and all, preferably are as thin as the membrane 48a at the lip region 39 of the cushion 30. At the lip region 39 the membranes have different thicknesses with, for instance membrane 46a being 0.06 inches thick, the membrane 47a being about 0.03 inches thick and membrane 48a being about 0.02 inches thick. The change in thickness of the membrane between the lip region 39 and the nasal bridge region 38 occurs in the cheek region 40. The advantages of the embodiment illustrated in FIGS. 6 and 7 as well as hereinafter is the use of the triple membrane system in combination with the varying thickness in the membrane in order to provide not only a soft feeling cushion but also an improved seal. As seen in FIG. 4, the area labeled "c" corresponds to the cheek region 40 and is the area where the membranes 46 and 47 are reduced in thickness until they all become the same thickness at the nasal bridge region 38 of the cushion 30. The area denoted in FIG. 4 as area "d" is the nasal bridge region 38 of the cushion 30 and it is in that region that the outer membrane 48b comes in contact with the bridge of the users nose and where for instance, the thickness of all membranes may be 0.02 inches.

As seen from FIG. 6, the thickness of the side wall 45a just above the channel 41 may be just slightly thicker than the thickness of the inner membrane 46a. Thereafter, the thickness of the side wall 45 diminishes from the inner membrane 46 to the outer membrane 48. Finally, the side wall 45 becomes the outer membrane 48. Also, the side wall 45a may be thicker at the lip region 39 than at 45b in the nasal bridge region 38. The variable thicknesses in the membranes 46, 47 and 48 are a significant feature of the invention and provide a significant improvement in the comfort of cushion 30, in use.

Preferably, the cushion 30 is a single piece of molded plastic and may be removably or fixedly secured to the cone or shell 15 as by sonic welding, adhesives or any other suitable means. Silicon plastics are well known in the art.

Figure 8:
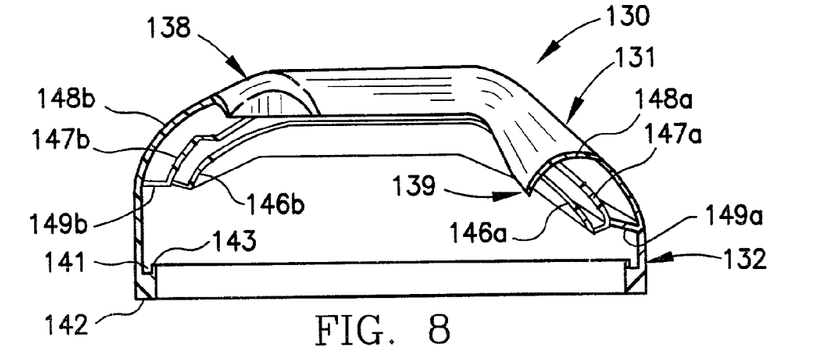
FIG. 8 is a cross-sectional view of another embodiment of the present invention as seen along line A—A of FIG. 4.
Figure 9:
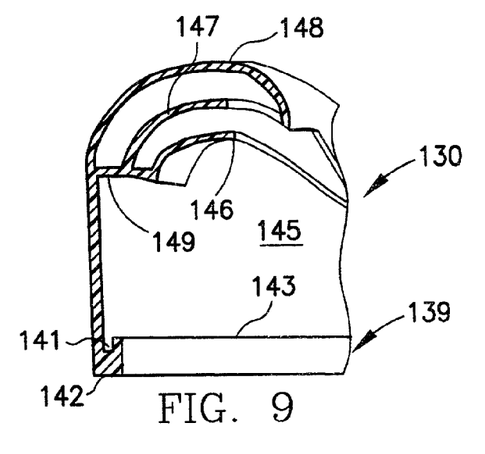
FIG. 9 is a cross-sectional view of the embodiment of FIG. 8 as seen along line B—B of FIG. 4.

Referring to FIGS. 8 and 9, there is shown another embodiment of the present invention in which cushion 130 is illustrated. Like numerals have been applied to like pieces with the exception that the embodiment of FIGS. 8 and 9 is identified with the corresponding number in the 100s. For instance, the outer surface of the cushion 130 is 131 as distinguished from the outer surface of the cushion 30 which is 31. The cushion 130 also has three membranes, the inner membrane 146, the middle membrane 147 and the outer membrane 148. The principal difference between the embodiments of FIGS. 6 and 7 and the embodiments of FIGS. 8 and 9 lies in the fact that the inner membrane 146 and the middle membrane 147 join to form a rib 149 connecting the membranes 146 and 147 to the side 145. Another difference in the embodiment of FIGS. 6 and 7 and the embodiment of FIGS. 8 and 9 is that the membranes 146, 147 and 148 do not change the thickness from the lip region 139 to the nasal bridge region 138.

Figure 10A:
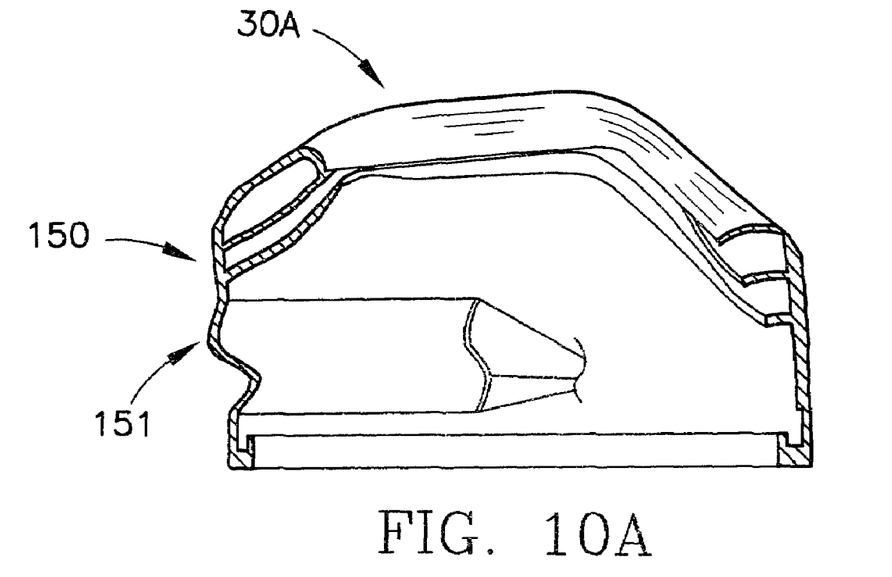
FIGS. 10A and 10B are views partly in section of an embodiment of the invention with an improved side wall.
Figure 10B:
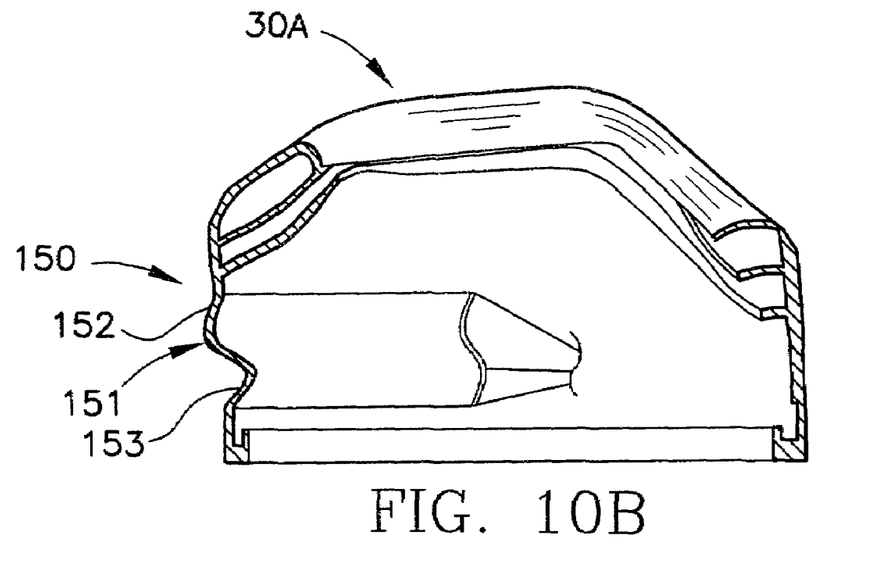
Figure 11:
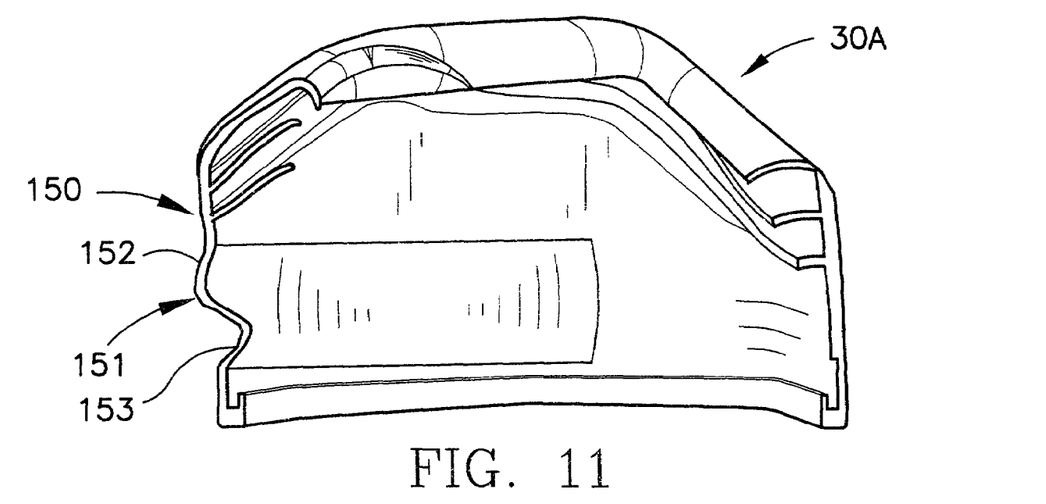
FIG. 11 is an elevational view partly in section of the embodiment of FIGS. 10A and 10B.

Referring now to FIGS. 10A and 10B and 11, there is disclosed a third embodiment of the present invention which is similar to the embodiment disclosed in FIGS. 6 and 7 except that the side wall 150 has a portion 151 which is other than straight. In the embodiment illustrated in FIGS. 10A and 10B and 11, the portion 151 which is other than straight includes two arcuate portions 152 and 153 which are joined to each other to form a sinuous portion 151. Although a sinuous portion 151 is shown in FIGS. 10A and 10B and 11, other designs are intended to be incorporated herein and covered by the claims and include, by way of example only, simple arcuate portions, curved portions, V-shaped portions, box or rectangular shaped cross-sections or any other than straight cross-section which provides a more compressible function to the side wall 150. The other than straight portion 151 of the side wall 150 is a significant improvement in the present invention in that the portion 151 is more compressible and provides a far improved sealing mechanism to the nasal bridge region of the cushion 30A. The remaining portions of the cushion 30A other than the side wall portion 151 is the same as shown in the embodiments illustrated in FIGS. 6 and 7. However, preferably the side wall portion 45A in FIG. 6 is extended somewhat as shown in FIGS. 10A and 10B and 11 and provides an improved angle of contact when the cushion 30A is worn by a user; and in the preferred embodiment is 1.95 inches in the lip region and 2.15 inches in the nasal bridge region.

As illustrated in the drawings of FIGS. 10A and 10B and 11, the other than straight portion 151 extends in a horse shoe configuration around the nasal bridge region of the cushion 30A and extends approximately 2/3 of the way along the side wall 150 from the nasal bridge region into the cheek region and toward the lip region of the cushion 30A. Although as illustrated in FIGS. 10A and 10B and 11, the other than straight portion 151 does not completely encircle the cushion 30A, there is no particular reason that it may not. Accordingly, it is intended to cover within the invention herein disclosed, an other than straight portion 151 which extends entirely around the cushion 30A as well as the embodiment illustrated in which the other than straight portion 151 eventually blends into the straight side wall portion near the lip region.

FIGS. 10A and 10B contains many actual measurements from one preferred embodiment of the present invention, but are included only for purposes of illustration and not by way of limitation.

While there has been disclosed what is considered to be the preferred embodiment of the present invention, it is understood that various changes in the details may be made without departing from the spirit, or sacrificing any of the advantages of the present invention.

We claim:

1. A nasal mask cushion to sealingly connect a mask to a wearer's face, the cushion comprising: a substantially triangularly-shaped frame of resilient material having a mask engaging portion and connected by a side wall to a face engaging portion with a nasal bridge region and a lip region; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein a portion of the side wall in the lip region is thicker than a portion of the side wall in the nasal bridge region.

2. A nasal mask cushion to sealingly connect a mask to a wearer's face, the cushion comprising: a substantially triangularly-shaped frame of resilient material having a mask engaging portion and connected by a side wall to a face engaging portion with a nasal bridge region and a lip region; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein the side wall in the lip region is shorter than the side wall in the nasal bridge region.

3. A nasal mask cushion to sealingly connect a mask to a wearer's face, the cushion comprising: a substantially triangularly-shaped frame of resilient material having a mask engaging portion and connected by a side wall to a face engaging portion; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein said first and second membranes are joined to one end of a common web having another end thereof joined to said side wall.

4. A nasal mask cushion to sealingly connect a mask to a wearer's face, the cushion comprising: a substantially triangularly-shaped frame of resilient material having a mask engaging portion and connected by a side wall to a face engaging portion; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein said membranes are joined to said side wall.

5. The cushion of claim 4, wherein at least a portion of the first membrane is thicker than a portion of the second membrane.

6. The cushion of claim 5, wherein the thickness of the outer membrane is substantially constant.

7. The cushion of claim 5, wherein at least a portion of the first and second membranes have substantially the same thickness.

8. The cushion of claim 7, wherein the portions of the first and second membranes having substantially the same thicknesses are in a nasal bridge region of the face engaging portion.

9. The cushion of claim 4, wherein at least a portion of the first membrane is thicker than a portion of the outer membrane.

10. The cushion of claim 9, wherein at least a portion of the first and outer membranes have substantially the same thickness.

11. The cushion of claim 10, wherein the portions of the first and outer membranes having substantially the same thickness are in a nasal bridge region of the face engaging portion.

12. The cushion of claim 4, wherein at least a portion of the second membrane is thicker than a portion of the outer membrane.

13. The cushion of claim 12, wherein at least a portion of the second and outer membranes have substantially the same thickness.

14. The cushion of claim 13, wherein the portions of the second and outer membranes having substantially the same thickness are in a nasal bridge region of the face engaging portion.

15. The cushion of claim 4, wherein at least a portion of the first membrane is thicker than a portion of said second membrane and a portion of said second membrane is thicker than a portion of said outer membrane.

16. The cushion of claim 15, wherein the portion of the membranes having different thickness are in the lip region of the face engaging portion.

17. The cushion of claim 15, wherein at least a portion of the first and second and outer membranes have substantially the same thickness.

18. The cushion of claim 17, wherein the portions of the membranes having substantially the same thickness are in the nasal bridge region and the portions of the membranes having different thicknesses are in a lip region of the face engaging portion.

19. A nasal mask cushion to sealingly connect a mask to a wearer's face, the cushion comprising: a substantially triangularly-shaped frame of resilient material having a mask engaging portion and connected by a side wall to a face engaging portion with a nasal bridge region and a lip region; at least a portion of said side wall between said frame and the nasal bridge region being other than straight to provide an improved sealing in the nasal bridge region; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein a portion of the side wall in the lip region is thicker than a portion of the side wall in the nasal bridge region.

20. A nasal mask cushion to sealingly connect a mask to a wearer's face, the cushion comprising: a substantially triangularly-shaped frame of resilient material having a mask engaging portion and connected by a side wall to a face engaging portion with a nasal bridge region and a lip region; at least a portion of said side wall between said frame and the nasal bridge region being other than straight to provide an improved sealing in the nasal bridge region; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein the side wall in the lip region is shorter than the side wall in the nasal bridge region.

21. A nasal mask cushion to sealingly connect a mask to a wearer's face, the cushion comprising: a substantially triangularly-shaped frame of resilient material having a mask engaging portion and connected by a side wall to a face engaging portion with a nasal bridge region; at least a portion of said side wall between said frame and the nasal bridge region being other than straight to provide an improved sealing in the nasal bridge region; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, wherein said first and second membranes are joined to one end of a common web having another end thereof joined to said side wall.

22. The cushion of claim 21, wherein the portion of said side wall that is other than straight is more compressible than at least a portion of said side wall between said frame and a lip region of the face engaging portion.

23. The cushion of claim 21, wherein the portion of said side wall that is other than straight is arcuate.

24. The cushion of claim 21, wherein the portion of said side wall that is other than straight is sinuous.

25. The cushion of claim 21, wherein at least a portion of the first membrane is thicker than a portion of the second membrane.

26. The cushion of claim 25, wherein the portion of the membranes having different thickness are in a lip region of the face engaging portion.

27. The cushion of claim 25, wherein at least a portion of the first and second membranes have substantially the same thickness.

28. The cushion of claim 27, wherein the portions of the first and second membranes having substantially the same thicknesses are in a nasal bridge region of the face engaging portion.

29. The cushion of claim 25, wherein the thickness of the outer membrane is substantially constant.

30. The cushion of claim 21, wherein at least a portion of the first membrane is thicker than a portion of the outer membrane.

31. The cushion of claim 30, wherein at least a portion of the first and outer membranes have substantially the same thickness.

32. The cushion of claim 31, wherein the portions of the first and outer membranes having substantially the same thickness are in a nasal bridge region of the face engaging portion.

33. The cushion of claim 21, wherein at least a portion of the second membrane is thicker than a portion of the outer membrane.

34. The cushion of claim 33, wherein at least a portion of the second and outer membranes have substantially the same thickness.

35. The cushion of claim 34, wherein the portions of the second and outer membranes having substantially the same thickness are in a nasal bridge region of the face engaging portion.

36. The cushion of claim 21, wherein at least a portion of the first membrane is thicker than a portion of said second membrane and a portion of said second membrane is thicker than a portion of said outer membrane.

37. The cushion of claim 36, wherein at least a portion of the first and second and outer membranes have substantially the same thickness.

38. The cushion of claim 37, wherein the portions of the membranes having substantially the same thickness are in a nasal bridge region of the face engaging portion and the portions of the membranes having different thicknesses are in a lip region of the face engaging portion.

39. A nasal mask cushion to sealingly connect a mask to a wearer's face, the cushion comprising: a substantially triangularly-shaped frame of resilient material having a mask engaging portion and connected by a side wall to a face engaging portion; a first membrane of resilient material having an inwardly extending rim substantially around said triangularly-shaped frame; a second membrane of resilient material spaced from and generally parallel to said first membrane and having a second inwardly extending rim; and an outer membrane of resilient material spaced from and generally parallel to said second membrane and having an outer inwardly extending rim, said outer membrane engaging a wearer's face in use, at least said first and second membranes being thicker in the lip region than said first and second and outer membranes in the nasal bridge region.

40. The cushion of claim 39, wherein at least a portion of said side wall between said frame and the nasal bridge portion being other than straight to provide an improved sealing in the nasal bridge region.

41. The cushion of claim 39, wherein the portion of said side wall that is other than straight is more compressible than at least a portion of said side wall between said frame and the lip region and there are three membranes.

42. The cushion of claim 39, wherein the portion of said side wall that is other than straight is arcuate.

43. The cushion of claim 39, wherein the portion of said side wall that is other than straight is sinuous.

44. A nasal mask cushion to sealingly connect a mask to a wearer's face, the cushion comprising: a substantially triangularly-shaped frame of resilient material having a mask engaging portion and connected by a side wall to a face engaging portion with a nasal bridge region and a lip region; a first membrane of resilient material having an inwardly extending rim substantially around said triangularly-shaped frame; one or more membranes of resilient material spaced from and generally parallel to said first membrane and having inwardly extending rims; one of said one or more outer membranes engaging a wearer's face in use, at least one of said first or one or more membranes being thicker in the lip region than said membranes in the nasal bridge region.

* * * * *